United States Patent

Kaufmann et al.

Patent Number: 5,099,025
Date of Patent: Mar. 24, 1992

[54] PREPARATION OF 2-CHLORO-5-METHYL-PYRIDINE

[75] Inventors: Dieter Kaufmann, Bergisch; Klaus Jelich, Wuppertal, both of Fed. Rep. of Germany

[73] Assignee: Bayer Aktiengesellschaft, Leverkusen, Fed. Rep. of Germany

[21] Appl. No.: 716,035

[22] Filed: Jun. 14, 1991

[30] Foreign Application Priority Data

Jun. 23, 1990 [DE] Fed. Rep. of Germany ....... 4020052

[51] Int. Cl.[5] .......................................... C07D 213/26
[52] U.S. Cl. ..................................... 546/345; 546/346
[58] Field of Search ................................. 546/345, 346

[56] References Cited

U.S. PATENT DOCUMENTS 4,897,488  1/1990  Gallenkamp et al. ............... 546/345
5,010,201  4/1991  Kaufmann et al. ................. 546/316

FOREIGN PATENT DOCUMENTS 0324174  7/1989  European Pat. Off. ............. 546/345
0370317  5/1990  European Pat. Off. ............. 546/345

OTHER PUBLICATIONS

Chemical and Pharmaceutical Bulletin, vol. 36, No. 6, 1988, pp. 2244–2247.

*Primary Examiner*—Alan L. Rotman
*Attorney, Agent, or Firm*—Sprung Horn Kramer & Woods

[57] ABSTRACT

A process for the preparation of 2-chloro-5-methylpyridine of the formula

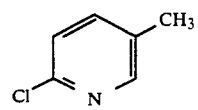

which comprises reacting 3-methyl-pyridine-1-oxide of the formula

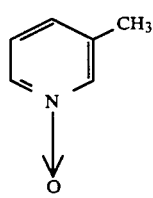

with a chlorinating agent of the formula

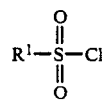

in which
R[1] represents alkyl, halogenoalkyl, cycloalkyl, optionally substituted aryl, NR[2]R[3] or OR[4] in which
R[2] and R[3] individually represent alkyl, cycloalkyl or aryl or together represent alkanediyl or oxaalkanediyl and
R[4] represents alkyl, cycloalkyl or optionally substituted aryl, in the presence of a basic organic nitrogen compound and in the presence of a diluent at a temperature between about −20° C. and +150° C.

12 Claims, No Drawings

PREPARATION OF 2-CHLORO-5-METHYL-PYRIDINE

The invention relates to a new process for the preparation of 2-chloro-5-methyl-pyridine.

It is known that 2-chloro-5-methyl-pyridine is obtained in addition to 2-chloro-3-methyl-pyridine, 4-chloro-3-methyl-pyridine and 3-chloro-5-methyl-pyridine when 3-methyl-pyridine-1-oxide is reacted with phosphoryl chloride (compare WeiBberger, Chemistry of Heterocyclic Compounds, Pyridine and its Derivatives, Vol. 14, Supplement, Part 2, p. 112). The principal product of this reaction is 4-chloro-3-methyl-pyridine; the proportion of 2-chloro-5-methyl-pyridine is in general below 25%.

It is further known that 2-chloro-5-methyl-pyridine is obtained when 3-methyl-pyridine-1-oxide is reacted with phosphoryl chloride in the presence of a basic organic nitrogen compound and in the presence of a diluent (compare EP-A 324,174). The use of phosphoryl chloride causes an amount of phosphorous-containing wastes to be formed, whose disposal is problematical.

A new process for the preparation of 2-chloro-5-methylpyridine of the formula (I)

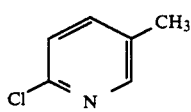

(I)

from 3-methyl-pyridine-1-oxide of the formula (II)

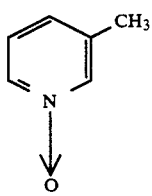

(II)

has now been found, which is characterized in that the reaction is carried out in the presence of a chlorinating agent of the general formula (III)

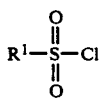

(III)

in which
R$^1$ represents alkyl, halogenoalkyl, cycloalkyl, optionally substituted aryl, NR$^2$R$^3$ or OR$^4$ in which
R$^2$ and R$^3$ individually represent alkyl, cycloalkyl or aryl or together represent alkanediyl or oxaalkanediyl, and
R$^4$ represents alkyl, cycloalkyl or optionally substituted aryl,
in the presence of a basic organic nitrogen compound and in the presence of a diluent at temperatures between −20° C. and +150° C., and the reaction product is worked up in the customary manner.

It is as surprising that 2-chloro-5-methylpyridine can be obtained by the process according to the invention in good yields, as the preparation of this and similar compounds using chlorinating agents of the formula (III) is not known and is also not suggested by previously disclosed processes.

The advantage of the process according to the invention compared to the known prior art is in particular that the chlorinating agents of the formula (III) and their conversion products can be disposed of without relatively large problems.

The process according to the invention thus represents a valuable enrichment of the prior art.

The course of the reaction in the process according to the invention can be outlined, for example, by the equation below:

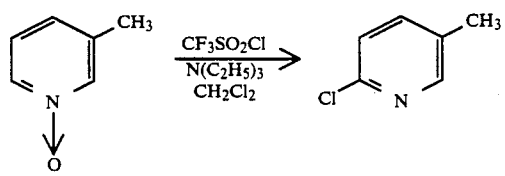

The starting compound of the formula (II) is already known (compare J. Am. Chem. Soc. 76 (1954), 1286–1291).

Formula (III) provides a general definition of the chlorinating agents to be used in the process according to the invention. In the formula (III)
R$^1$ preferably represents alkyl (C$_1$–C$_6$), halogenoalkyl (C$_1$–C$_6$), cycloalkyl (C$_3$–C$_7$), phenyl or naphthyl which are optionally substituted by halogen and/or alkyl (C$_1$–C$_6$), NR$^2$R$^3$ or OR$^4$,
in which
R$^2$ and R$^3$ individually represent alkyl (C$_1$–C$_6$), cycloalkyl (C$_3$–C$_6$) or phenyl or together represent alkanediyl (C$_2$–C$_6$) or oxaalkanediyl (C$_2$–C$_5$) and
R$^4$ represents alkyl (C$_1$–C$_6$), cycloalkyl (C$_3$–C$_7$), phenyl or naphthyl which are optionally substituted by halogen and/or alkyl (C$_1$–C$_4$).

In the formula (III)
R$^1$ in particular represents alkyl (C$_1$–C$_4$), perfluoroalkyl (C$_1$–C$_6$), perchloroalkyl (C$_1$–C$_6$), cycloalkyl (C$_5$–C$_6$), phenyl, phenyl which is substituted by halogen and/or alkyl (C$_1$–C$_4$), naphthyl, naphthyl which is substituted by halogen and/or alkyl (C$_1$–C$_4$), or NR$^2$R$^3$ or OR$^4$,
in which
R$^2$ and R$^3$ individually represent methyl, ethyl, propyl, isopropyl, butyl, isobutyl, cyclopentyl, cyclohexyl or phenyl or together represent butane-1,4-diyl (tetramethylene), pentane-1,5-diyl (pentamethylene) or 3-oxapentane-1,5-diyl (—CH$_2$CH$_2$—O—CH$_2$CH$_2$—),
and in which
R$^4$ represents alkyl (C$_1$–C$_6$), cycloalkyl (C$_5$–C$_6$), phenyl or naphthyl which are optionally substituted by chlorine and/or methyl.

Very particularly preferred chlorinating agents of the formula (III) are those in which
R$^1$ represents perfluoroalkyl (C$_1$–C$_6$), perchloroalkyl (C$_1$–C$_6$), phenyl, naphthyl or dialkylamino NR$^2$R$^3$,
in which
R$^2$ and R$^3$ represent methyl, ethyl, propyl or butyl.

The following may be mentioned as examples of the chlorinating agents of the formula (III):
trifluoromethyl-sulphonyl chloride
nonafluorobutyl-sulphonyl chloride
perfluorohexyl-sulphonyl chloride
trichloromethyl-sulphonyl chloride phenyl-sulphonyl chloride
4-chlorophenyl-sulphonyl chloride
2-chlorophenyl-sulphonyl chloride
2,5-dichlorophenyl-sulphonyl chloride
2-methylphenyl-sulphonyl chloride
1-naphthyl-sulphonyl chloride
2-naphthyl-sulphonyl chloride
1,5-naphthalene-di-sulphonyl chloride
2,6-naphthalene-di-sulphonyl chloride
N,N-dimethyl-sulphamoyl chloride
N,N-diethyl-sulphamoyl chloride
N,N-dipropyl-sulphamoyl chloride
N,N-dibutyl-sulphamoyl chloride The compounds of the formula (III) are known and/or can be prepared by processes which are known per se (compare for this Houben-Weyl, Volume 9, G. Thieme Verlag, 1955, p.343 et seq., p.557 et seq.).

If an alkyl- or arylsulphonyl chloride is used as the chlorinating agent (III) in the process according to the invention, then $R^1$ preferably represents methyl, ethyl, n-propyl, i-propyl, n-butyl, i-butyl, tert.-butyl, n-amyl, i-amyl, cyclopentyl, cyclohexyl, trifluoromethyl, pentafluoroethyl, heptafluoropropyl, nonafluorobutyl, trichloromethyl, phenyl, toluyl, xyloyl, chlorophenyl, dichlorophenyl, naphthyl, 1,5-naphthdiyl or 2,6-naphthdiyl.

If an alkyl or aryl chlorosulphonate is used as the chlorinating agent (III) in the process according to the invention, then $R^1$ represents the group $OR^4$, where $R^4$ preferably represents methyl, ethyl, n-propyl, i-propyl, n-butyl, i-butyl, tert.-butyl, n-amyl, i-amyl, cyclopentyl, cyclohexyl, phenyl, tolyl, xylyl, chlorophenyl or naphthyl.

If a sulphamoyl chloride is used as the chlorinating agent (III) in the process according to the invention, then $R^1$ represents the group $NR^2R^3$, where $R^2$ and $R^3$ individually preferably represent $C_1$–$C_6$-alkyl, $C_5$–$C_6$-cycloalkyl or phenyl or where $R^2$ and $R^3$ together represent $C_2$–$C_6$-alkanediyl or $C_2$–$C_5$-oxaalkanediyl.

The process according to the invention is carried out in the presence of a basic nitrogen compound. Preferred basic organic nitrogen compounds are dialkylamines, such as, for example, diethylamine, dipropylamine, diisopropylamine, dibutylamine, diisobutylamine and di-sec-butylamine, trialkylamines, such as, for example, trimethylamine, triethylamine, tripropylamine and tributylamine, methyldiisopropylamine, ethyldiisopropylamine, dialkylcycloalkylamines, such as, for example, dimethylcyclopentylamine, diethyl-cyclopentylamine, dimethylcyclohexylamine and diethylcyclohexylamine, dialkylaralkylamines, such as, for example, dimethyl-benzylamine and diethyl-benzylamine and dialkylarylamines, such as, for example, dimethylaniline.

Particularly preferred basic organic nitrogen compounds are trialkylamines, such as, for example, trimethylamine, triethylamine, tripropylamine, tributylamine, methyldiisopropylamine and ethyldiisopropylamine.

The process according to the invention is carried out in the presence of a diluent. Suitable diluents are virtually all the inert organic solvents. These preferably include optionally halogenated hydrocarbons, such as pentane, hexane, heptane, octane, cyclohexane, methylcyclohexane, petroleum ether, benzine, ligroin, benzene, toluene, xylene, methylene chloride, chloroform, tetrachloromethane, 1,2-dichloroethane, 1,1,2-trichloroethane, 1,2-dichloropropane, 1,2,3-trichloropropane, chlorobenzene and dichlorobenzene, ethers, such as diethyl ether, dipropyl ether, diisopropyl ether, dibutyl ether, methyl tert.-butyl ether, methyl tert.-amyl ether, glycol dimethyl ether, diglycol dimethyl ether, tetrahydrofuran, dioxane and anisole, ketones, such as acetone, methyl ethyl ketone, diethyl ketone, methyl isopropyl ketone and methyl isobutyl ketone, esters, such as methyl acetate, ethyl acetate, propyl acetate, butyl acetate and amyl acetate, nitriles, such as acetonitrile and propionitrile, amides such as dimethylformamide, dimethylacetamide and N-methyl-pyrrolidone, and also dimethyl sulphoxide and sulpholane.

The reaction temperatures in the process according to the invention can be varied within a relatively wide range. In general, the reaction is carried out at temperatures between $-20°$ C. and $+150°$ C., preferably at temperatures between $0°$ C. and $+80°$ C.

The process according to the invention is in general carried out under normal pressure. However, it is also possible to work at elevated or reduced pressure of between 0.1 and 10 bar.

In order to carry out the process according to the invention, between 1 and 10 moles, preferably between 1.5 and 4.0 moles, of chlorinating agent of the formula (III) and also between 1 and 10 moles, preferably between 1.5 and 4.0 moles, of the basic organic nitrogen compound are in general employed per mole of 3-methyl-pyridine-1-oxide of the formula (II).

In a preferred embodiment of the process according to the invention, the 3-methyl-pyridine-1-oxide and the basic organic nitrogen compound are initially introduced in a diluent and the chlorinating agent of the formula (III) is then slowly metered in with stirring. The complete reaction mixture is then optionally further stirred until the reaction is complete.

Working-up can be carried out in a customary manner. For example, the reaction mixture is diluted with water and optionally rendered neutral with sodium hydroxide solution, and the organic phase is separated off. Further product is extracted from the aqueous phase using an organic solvent, such as, for example, methylene chloride. The combined organic phases are dried and filtered; the solvent is carefully removed from the filtrate by distillation in a water jet vacuum.

The residue which remains essentially contains the product of the formula (I), which may be further purified in a customary manner, for example by vacuum distillation.

The 2-chloro-5-methyl-pyridine which can be prepared by the process according to the invention is known as an intermediate for pharmaceuticals (compare DE-A 2,812,585), but can also be employed as an intermediate for insecticides (compare DE-A 2,630,046).

PREPARATION EXAMPLE 1

2-Chloro-5-methyl-pyridine

A solution of 12.6 g (75 mmol) of trifluoromethanesulphonyl chloride in 20 ml of methylene chloride is added dropwise under nitrogen in the course of 20 min to a solution of 5.5 g (50 mmol) of 3-methylpyridine-1-oxide and 7.6 g (75 mmol) of triethylamine in 80 ml of methylene chloride. The mixture is then heated under reflux for a further 12 hours, the solid is then filtered off with suction and the filter cake is washed with methylene chloride. The methylene chloride solution is stirred with conc. hydrochloric acid, and the aqueous phase is separated off, rendered neutral using sodium hydroxide solution and extracted using methylene chloride. After removing the solvent by distillation, a residue remains which is analyzed by gas chromatography.

Yield: 3.82 g (60%) of a mixture of 80% 2-chloro-5-methylpyridine and 20% 2-chloro-3-methylpyridine.

The pure 2-chloro-5-methyl-pyridine can be separated off by fractional distillation.

PREPARATION EXAMPLE 2

2-Chloro-5-methyl-pyridine

A solution of 76.2 g (0.4 mol) of p-tolunesulphonyl chloride in 150 ml of methylene chloride is added dropwise under nitrogen in the course of 70 min to a solution of 21.8 g (0.2 mol) of 3-methylpyridine-1-oxide and 40.4 g (0.4 mol) of triethylamine in 150 ml of methylene chloride. The mixture is then heated under reflux for a further 12 hours, the solid is then filtered off with suction, the filter cake is washed with 50 ml of methylene chloride and the solvent is removed by distillation. The bottom is subjected to a steam distillation at a pH of 6. The distillate is extracted three times using 100 ml of methylene chloride each time. After removing the solvent by distillation, a residue remains which is analyzed by gas chromatography.

Yield: 13.2 g (52%) of a mixture of 70% 2-chloro-5-methylpyridine and 30% 2-chloro-3-methylpyridine.

The pure 2-chloro-5-methyl-pyridine can be separated off by fractional distillation.

PREPARATION EXAMPLE 3

2-Chloro-5-methyl-pyridine

A solution of 20 g (0.1 mol) of N,N-dipropylsulphamoyl chloride in 60 ml of chlorobenzene is added dropwise under nitrogen to a solution of 5.5 g (50 mmol) of 3-methylpyridine-1-oxide and 10.1 g (0.1 mol) of triethylamine in 40 mol of chlorobenzene. The mixture is then heated to 70° C. for a further 3 hours, the solid is then filtered off with suction, the filter cake is washed with chlorobenzene and the liquid phase is extracted using conc. hydrochloric acid. The aqueous phase is rendered neutral using sodium hydroxide solution and extracted using toluene. After removing the solvent by distillation, a residue remains which is analyzed by gas chromatography.

Yield: 3.37 g (53%) of a mixture 80% 2-chloro-5-methylpyridine and 20% 2-chloro-3-methylpyridine.

The pure 2-chloro-5-methyl-pyridine can be separated off by fractional distillation.

It will be understood that the specification and examples are illustrative but not limitative of the present invention and that other embodiments within the spirit and scope of the invention will suggest themselves to those skilled in the art.

We claim:

1. A process for the preparation of 2-chloro-5-methylpyridine of the formula

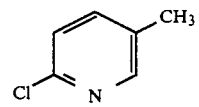

(I)

which comprises reacting 3-methyl-pyridine-1-oxide of the formula

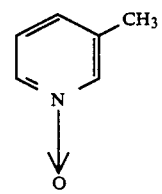

(II)

with a chlorinating agent of the formula

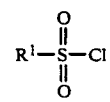

(III)

in which $R^1$ represents alkyl, halogenoalkyl, cycloalkyl, optionally substituted aryl, $NR^2R^3$ or $OR^4$ in which $R^2$ and $R^3$ individually represent alkyl, cycloalkyl or aryl or together represent alkanediyl or oxaalkanediyl and $R^4$ represents alkyl, cycloalkyl or optionally substituted aryl, in the presence of a basic organic nitrogen compound and in the presence of a diluent at a temperature between about —20° C. and +150° C.

2. The process according to claim 1, in which $R^1$ represents alkyl ($C_1$-$C_6$), halogenoalkyl ($C_1$-$C_6$), cycloalkyl ($C_3$-$C_7$), phenyl or naphthyl which are optionally substituted by halogen and/or alkyl ($C_1$-$C_6$) $NR^2R^3$ or $OR^4$, in which $R^2$ and $R^3$ individually represent alkyl ($C_1$-$C_6$), cycloalkyl ($C_3$-$C_6$) or phenyl or together represent alkanediyl ($C_2$-$C_6$) or oxaalkanediyl ($C_2$-$C_5$) and $R^4$ represents alkyl ($C_1$-$C_6$), cycloalkyl ($C_3$-$C_7$), phenyl or naphthyl which are optionally substituted by halogen and/or alkyl ($C_1$-$C_4$).

3. The process according to claim 1, in which $R^1$ represents methyl, ethyl, n-propyl, i-propyl, n-butyl, i-butyl, tert.-butyl, n-amyl, i-amyl, cyclopentyl, cyclohexyl, trifluoromethyl, pentafluoroethyl, heptafluoropropyl, nonafluorobutyl, trichloromethyl, phenyl, toluyl, xyloyl, chlorophenyl, dichlorophenyl, naphthyl, 1,5-naphthdiyl or 2,6-naphthdiyl.

4. The process according to claim 1, in which $R^4$ represents methyl, ethyl, n-propyl, i-propyl, n-butyl, i-butyl, tert.-butyl, n-amyl, i-amyl, cyclopentyl, cyclohexyl, phenyl, toluyl, xyloyl, chlorophenyl or naphthyl.

5. The process according to claim 1, in which $R^1$ represents the group $NR^2R^3$, in which $R^2$ and $R^3$ individually represent $C_1-C_6$-alkyl, $C_5-C_6$-cycloalkyl or phenyl or together represent $C_2-C_6$-alkanediyl or $C_2-C_5$-oxaalkanediyl.

6. The process according to claim 1, wherein the reaction is carried out in the presence of a basic organic nitrogen compound selected from the group consisting of a dialkylamine, trialkylamine, dialkyl-cycloalkylamine, dialkyl-aralkylamine and dialkyl-arylamine.

7. The process according to claim 1, wherein the reaction is carried out in the presence of a basic organic nitrogen compound selected from the group consisting of diethylamine, dipropylamine, diisopropylamine, dibutylamine, diisobutylamine, di-sec-butylamine, trimethylamine, triethylamine, tripropylamine, tributylamine, methyldiisopropylamine, ethyldiisopropylamine, dimethyl-cyclopentylamine, diethyl-cyclopentylamine, dimethyl-cyclohexylamine, dimethylbenzylamine, diethylbenzylamine and dimethylaniline.

8. The process according to claim 1, wherein the reaction is carried out in the presence of an inert organic solvent as diluent.

9. The process according to claim 1, wherein the reaction is carried out in the presence of methylene chloride, ethylene chloride, 1,1,2-trichloroethane, 1,2-dichloropropane 1,2,3-trichloropropane or chlorobenzene as diluent.

10. The process according to claim 1, wherein the reaction is carried out at a temperature between 0° C. and +80° C.

11. The process according to claim 1, wherein between 1 and 10 moles of chlorinating agent and between 1 and 10 moles of the basic organic nitrogen compound are employed per mole of 3-methyl-pyridine-1-oxide.

12. The process according to claim 1, wherein the 3-methyl-pyridine-1-oxide and the basic nitrogen compound are initially introduced into a diluent and the chlorinating agent is slowly metered in with stirring, and the complete reaction mixture is optionally further stirred until the reaction is complete.

* * * * *